(12) United States Patent
Lee et al.

(10) Patent No.: US 6,900,056 B2
(45) Date of Patent: May 31, 2005

(54) CHEMICALLY DEFINED MEDIUM FOR CULTURED MAMMALIAN CELLS

(75) Inventors: ChiChang Lee, Norristown, PA (US); Celia Ly, Lancaster, PA (US); Gordon Moore, Wayne, PA (US); Robert Perkinson, Philadelphia, PA (US)

(73) Assignee: Centocor, Inc., Malvern, PA (US)

( * ) Notice: Subject to any disclaimer, the term of this patent is extended or adjusted under 35 U.S.C. 154(b) by 242 days.

(21) Appl. No.: 10/067,382

(22) Filed: Feb. 5, 2002

(65) Prior Publication Data

US 2003/0096402 A1 May 22, 2003

Related U.S. Application Data

(60) Provisional application No. 60/268,849, filed on Feb. 15, 2001.

(51) Int. Cl.[7] .................................................. C12N 5/00
(52) U.S. Cl. ...................... 435/404; 435/405; 435/406
(58) Field of Search ................................ 435/404, 405, 435/406

(56) References Cited

U.S. PATENT DOCUMENTS

| 4,205,126 | A | * | 5/1980 | Cartaya |
| 4,767,704 | A | * | 8/1988 | Cleveland et al. |
| 5,691,203 | A | * | 11/1997 | Katusen et al. |
| 5,814,511 | A | | 9/1998 | Chang et al. |
| 6,194,203 | B1 | * | 2/2001 | Blum et al. |
| 6,399,381 | B1 | * | 6/2002 | Blum et al. |

FOREIGN PATENT DOCUMENTS

WO   WO 02/101019 A 2   12/2002

OTHER PUBLICATIONS

PCT International Search Report PCT/US02/03274 dated Sep. 18, 2002.

* cited by examiner

Primary Examiner—Leon B. Lankford, Jr.

(57) ABSTRACT

The present invention relates to methods and compositions for chemically defined media for growth of mammalian cells for production of commercially useful amounts of expressed proteins.

3 Claims, 2 Drawing Sheets

CHEMICALLY DEFINED MEDIUM FOR CULTURED MAMMALIAN CELLS

FIELD OF THE INVENTION

This application is based in part on, and claims priority to, U.S. Provisional No. 60/268,849 filed Feb. 15, 2001, of which is entirely incorporated herein by reference.

The present invention in the field of biotechnology, relates to methods and compositions for providing chemically defined media for growth of cultured mammalian cells for production of commercially useful amounts of expressed proteins.

BACKGROUND OF THE INVENTION

Bovine serum is commonly used in mammalian cell culture to promote cell growth and protein production. Since serum is expensive, non-defined animal materials such as primatone and albumin have been used as serum replacements. However, the quality of these non-defined animal proteins varies from batch to batch and consistent cell growth in these media is difficult to achieve. Moreover, pathogens such as prions and viruses have been identified as potential infectious agents (Balter, M. 2000, Kozak et al. 1996) that may reside in those animal derived products. Many regulations now strongly address these concerns about using serum or non-defined animal proteins in mammalian cells.

To support the growth of animal cells, a variety of components are essential to be included in the culture media. For example, glutamine and glucose are basic energy sources that support animal cell growth. Breakdown of these compounds provides resources for energy-generating pathways, the TCA cycle and glycolysis. The byproducts of these pathways are also the building blocks or sources for bio polymer synthesis (Petch and Bulter 1994). In addition, vitamins, amino acids and growth factors are also essential for robust cell growth by either supressing the cascade of the suicide pathway known as apoptosis or by promoting the progression of the cell cycle so that cells may replicate (Franek F. 1994, Murakami et al. 1982, Mastrangelo et al. 1999, Xie and Wang, 1996, Muhamed Al-Rubeai 1998).

Trace elements are also important for the growth of animal cells. Ham and McKeehan (1979) noticed that adding trace elements, such as Zinc, iron, selenium, copper, molybdenum, and manganese, etc., was important for cloning and continuous passage of animal cells in stringent conditions of serum-free media. Regardless, the importance of supplementing trace elements in the media for animal cells has not been well addressed (Schneider 1989, Merten and Litwin 1991). This may be due to the assumption that trace elements existed as contaminated impurities within serum or non-defined animal derived materials already.

Accordingly, there is also a need to provide chemically defined media for cell culture and/or production of heterologous proteins in commercially useful amounts.

SUMMARY OF INVENTION

The present invention provides chemically defined media (CDF) formulations and methods that provide certain compounds, amino acids, lipids, carbohydrates, trace elements and/or vitamins that provide a chemically defined media that excludes the use of non-defined animal derived raw materials (e.g., but not limited to, primatone, albumin and Excyte™, as well as other similar materials derived from serum or other animal derived proteins or products). Such media compositions and formulations of the present invention allow the growth of myeloma and other cell cultures to provide commercially useful amounts of the desired proteins expressed in such cell cultures. Accordingly the present invention provides specific media, formulations and methods of making and using thereof, as well as proteins provided therefrom. The present invention provides media that provide one or more advantages of being chemically defined, better protein producing, commercially suitable, cost-effective, and/or pose reduced regulatory concerns for proteins produced in cell lines grown therein.

Figure 1:
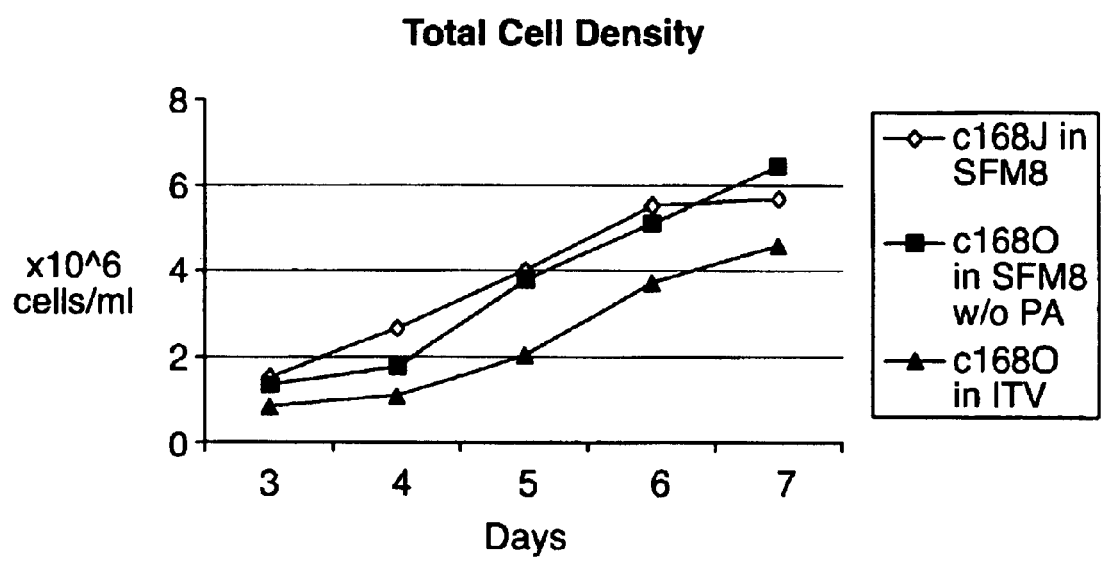
FIG. 1 shows by graphical representation that CDM media of the present invention can support high cell density up to $4.5 \times 10^6$ cells/mL on Day 7.
Figure 2:
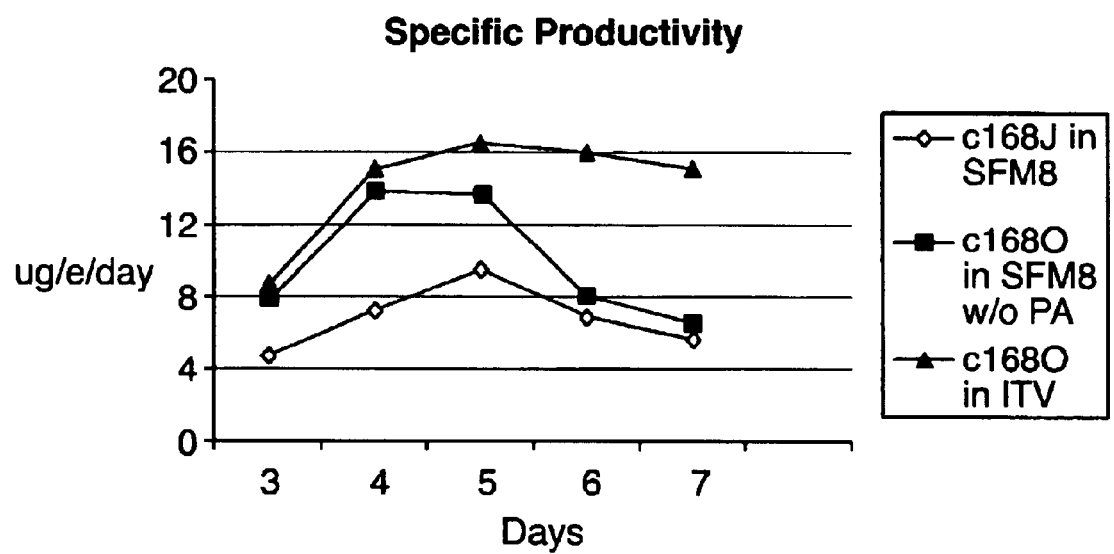
FIG. 2 shows by graphical representation that specific productivity for CDM culture is at 16 $\mu$g/$10^6$ cells/day.
Figure 3:
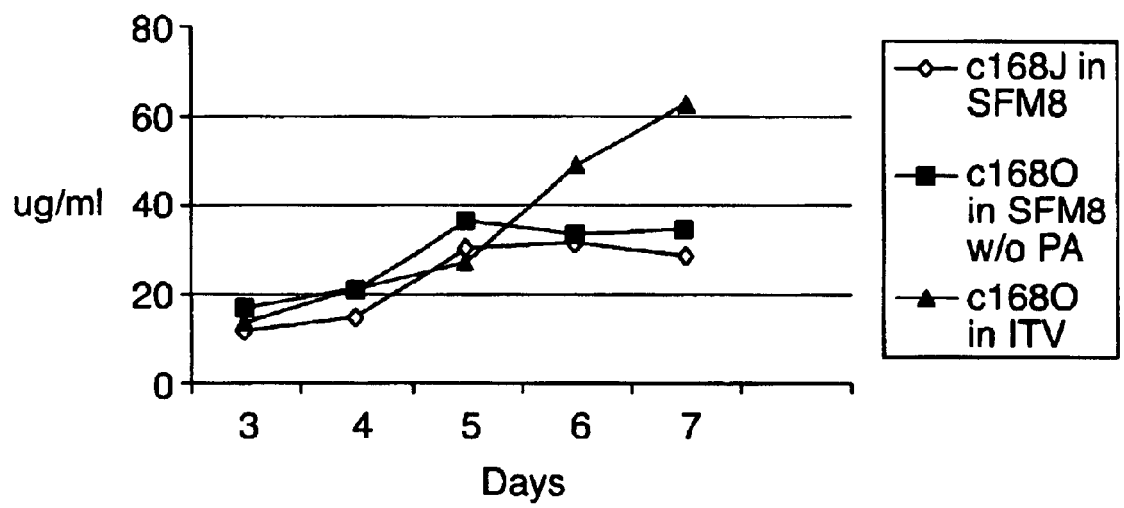
FIG. 3 shows that at high cell density between $4-5 \times 10^6$ cells/mL, IgG production reached above 60 $\mu$g/mL.
Figure 4:
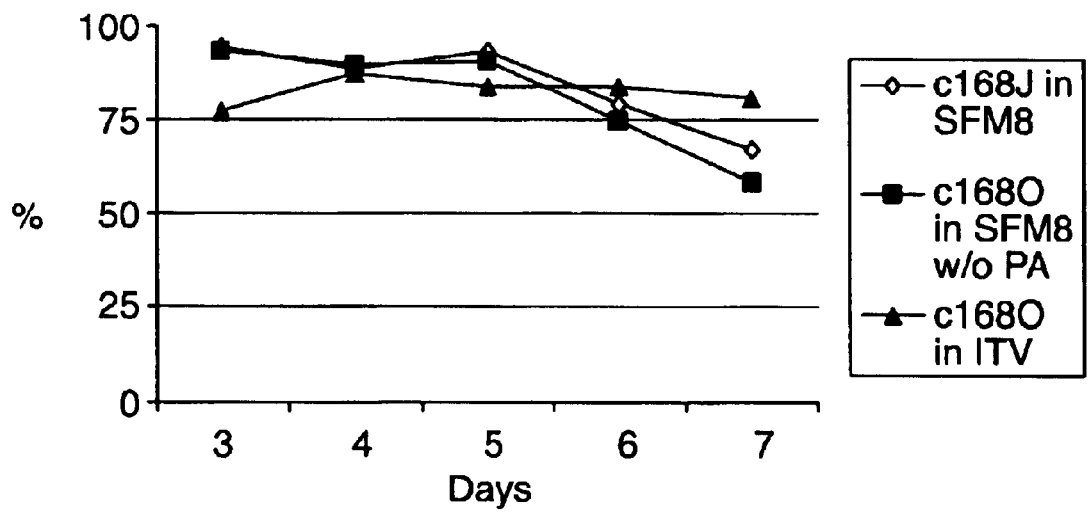
FIG. 4 shows by graphical representation that Viability of the CDM spinner culture remained above 75% throughout the experiment.

Also included in FIGS. 1–4 are data of C168O in SFM8 without primatone, albumin and C168J in SFM8 as references for comparison.

DETAILED DESCRIPTION

The present invention provides media formulations and methods that provide a chemically defined media that provides advantages over known media, and which can be used for commercial production of mammalian cell-cultured proteins. The present invention also provides a chemically defined media (CDM) comprising novel components, as well as, or optionally further comprising, at least one of specified amino acids, lipids, carbohydrates, trace elements, vitamins, compounds and/or proteins, as described and enabled herein, in combination with what is known in the art.

The present invention avoids of one or more problems associated with media that contains animal derived, or non-defined animal derived, components (e.g., but not limited to, primatone, albumin and excyte, as well as other similar materials derived from serum or other animal proteins in recombinant, synthetic or purified form).

Accordingly, chemically defined media (CDM) compositions and formulations of the present invention allow the growth of myeloma and other cell cultures to provide commercially useful amounts of the desired proteins expressed in such cell cultures. The present invention thus provides specific media formulations that are chemically defined, cost-effective, and pose reduced regulatory concerns compared to known media that comprise animal-derived materials that are not completely defined, or known chemically defined media.

Media of the present invention includes the substitution of specified components, without the use of animal derived proteins. In a preferred embodiment, media of the present invention comprises specified components, e.g., but not limited to, trace elements and vitamins, the media termed "chemically defined media" (CDM). Media of the present invention provides utility and improvements, including, but not limited to, at least one of suitable high cell density growth, improved growth rate, improved growth in scale up, improved viability, improved viability in scale up, improved protein yield, improved protein yield in scale up, and the like.

Suitable cell lines that can be used according to the present invention include any transformed or immortalized mammalian cell line. Such cell lines can include myeloma cell lines, such as Sp2/0, NSO, NS1, CHO, BHK, Ag653, P3X63Ag8.653 cells (ATCC Accession Number CRL-1580) and SP2/0-Ag14 cells (ATCC Accession Number CRL-1851), COS-1 (e.g., ATCC CRL 1650), COS-7 (e.g., ATCC CRL-1651), HEK293, BHK21 (e.g., ATCC CRL-10), CHO (e.g., ATCC CRL 1610, CHO DXB-11, CHO DG44), BSC-1 (e.g., ATCC CRL-26) cell lines, HepG2 cells, P3X63Ag8.653, 293 cells, HeLa cells, NIH 3T3, COS-1, COS-7, NIH 273, and the like, or any cells derived therefrom, including cell fusions of the above, such as to protein producing cells, such as B-cells, antibody producing cells, isolated or cloned spleen or lymph node cells, and the like. A preferred cell line is derived from Sp2/0 and is designated C463A, as described herein.

Cell lines, such as those presented herein, can be adapted to a chemically defined media according to the present invention, using known techniques and/or as described herein. Such methods can take from 1–30 days, or up to several months, depending on the particular cell line and media formulation used. However, adaption of mammalian cells to grow in chemically defined media of the present invention is unexpectedly found to occur in significantly shorter times that known defined or undefined media.

At least one formulation of media of the present invention is unexpectedly discovered to provide at least one of several advantages over known media, including at least one of: (1) supporting improved or robust growth and protein or antibody production from various mammalian cell lines; (2) facilitated adaptation for protein producing cell lines; (3) cost-effective media components, as compared to known components, such as bovine serum and excyte, which do not need to be and are not included; and/or (4) better suitability for regulatory approval as the media components are at least one of better defined, do not include animal derived proteins or other products, and do not contain or potentially contain infectious agents.

The use of this medium in cell culture technologies, such as but not limited to culture dishes, culture plates, culture bottles, suspension culture, spin filter suspension culture, bioreactors, perfusion type bioreactors, mammalian cell fermentation culture, or any other suitable type of cell culture, is also included in the present invention.

A media formulation of the present invention includes at least one of specified buffers, salts, carbohydrates, vitamins, proteins, amino acids, lipids, trace elements, minerals, and the like as described herein in combination with what is known in the art.

The media preferably comprises, in addition to known mammalian or hybridoma cell culture components without undefined protein- or animal-derived components, at least one or more of ammonium metavanadate, cadmium chloride, chromic potassium sulfate, ferric citrate, germanium dioxide, molybdic acid, salt or ammonium salt, nickel sulfate, zirconium chloride and/or hydrocortisone, or any suitable form, salt, halide, hydrate, solution, suspension, emulsion, or colloid thereof, powder and the like. In preferred embodiments, the media comprises, in addition to known components, at least one, two, three, four, five, six, seven, eight, or nine of the above components.

Non-limiting examples of such buffers and include at least one of MOPS, sodium phosphate, potassium phosphate, HEPES, and other known buffers. Salts included in such buffers include, but are not limited to sodium chloride, potassium chloride, and the like. Non-limiting examples are presented as one or more of the salts, as hydrous, anhydrous or other salt form, in the following table:

| Component | g/L |
|---|---|
| INORGANIC SALTS | |
| AlCl3.6H2O | 0.0000001–0.00001 |
| NH4Vo$_3$ | 0.00000006–0.000001 |
| BaCl$_2$ | 0.0000002–0.000001 |
| CaCl2.2H2O | 0.004–0.09 |
| CoCl2.6H2O | 0.0000002–0.00001 |
| CrK(So4)$_2$ | 0.0000001–0.00001 |
| CuSo4.5H2O | 0.0000005–0.00001 |
| FeSo4.7H2O | 0.000001–0.0001 |
| Geo$_2$ | 0.00000005–0.000001 |
| LiCl | 0.001–0.1 |
| MgCl.6H2O | 0.01–1.0 |
| MnCl(anhyd) | 0.00000001–0.000001 |
| Na2Moo4.2H2O | 0.00000001–0.000001 |
| NiNo3.6H2O | 0.00000002–0.000001 |
| KBr | 0.00000001–0.000001 |
| KCl | 0.01–1.0 |
| KI | 0.00000001–0.000001 |
| RbCl | 0.000000001–0.0000001 |
| AgCl | 0.0000000004–0.0000001 |
| NaHCO$_3$ | 0.0000001–0.00001 |
| NaCl | O.1–50 |
| NaF | 0.0000004–0.00001 |
| Na2HPo$_4$(anhyd) | 0.01–5 |
| Na2Seo$_3$ | 0.000003–0.0001 |
| SnCl2.2H2O | 0.00000001–0.000001 |
| Tio$_2$ | 0.0000001–0.0001 |
| ZnSo4.7H2O | 0.000008–0.0001 |

Such carbohydrates include, but are not limited to, glucose (dextrose), fructose, mannose, galactose, and any other suitable monosaccharide, disaccharide, polysaccharide, polymer, carbohydrate and the like. Non-limiting examples of amounts include 0.0000001–100 g/L for one or more carbohydrate components.

Such vitamins and co-factors can include, but are not limited to, biotin, ascorbic acid, pantothenate, choline, folate, inositol, niacin, niacinamide, pyridoxal, riboflavin, thamine, cyanocbalamin, L-abscorbic acid and salts, D-biotin, calciferol, choline, cocarboxylase, coenzyme A, 2-deoxyadenosine, 2-deoxyguanosine, 2-deoxycytidine, ergocalciferol, flavin adenosine dinucleotide, FAD, folic acid, D-glucoronic acid, lactone, D-glucoronic acid, glutathione, myo-inositol, mammalian recombinant insulin, menadione, 5'methylcytosine, niacinamide, NADP, NAD, nicotinic acid, oxalacetic acid, p-amino benzoic acid, D-pantothenic acid, pyroxidal, pyroxidine, retinol acetate, riboflavin, α-tocopherol, thiamine, thymidine, UMP, UDP, UTP, AMP, ADP., ATP, GMP, GDP, GTP, CMP, CDP, CTP, TMP, TDP, TTP, vitamin B12, and the like, in any suitable form, such as salt, acid, base, and the like.

Such proteins or amino acids include, but are not limited to, alanine, arginine, asparagine, aspartate, cysteine, cystine, glutamine, glutamate, glycine, histidine, isoleucine, leucine, lysine, methionine, phenylalanine, proline, serine, threonine, tryptophan, tyrosine, valine, and salts or other derivatives thereof. Alternatively, such amino acids include at least one of L-α-amino-n-butyric acid, L-alanine, L-arginine, L-aspartic acid, L-asparagine, L-cysteine, L-citrulline, L-cysteine, D-glucosamine, L-glutamic acid, L-glutamine, L-glycine, L-histidine, hydroxy-L-Proline, L-isoleucine, L-leucine, L-lysine, L-methionine, L-ornithine, L-omithine, L-phenylalanine, L-proline, L-serine, taurine, L-threonine, L-tryptophan, L-tyrosine, L-valine, and the like, as well as salts, hydrates, hydrides, acids, bases thereof and the like.

Such trace elements and minerals include, but are not limited to, salts (e.g., chlorides, iodides, bromides, fluorides, sodium or potassium salts, phosphates, salts, and the like), acids (e.g., acetates, sulfates, sulfides, nitrates, nitrides, dioxides, and the like), bases (e.g., NaOH, KOH, and the like), of magnesium, potassium, sodium, calcium, and the like, such as sodium acetate, sodium chloride, sodium phosphate, selenium, aluminum, ammonium metavanadate, barium, cadmium, cobalt chloride, chromic potassium sulfate, cupric sulfate, ferric citrate, germanium dioxide, lithium chloride, magnesium chloride, manganese chloride, molybdic acid, nickel nitrate, potassium bromide, potassium iodide, rubidium chloride, silver chloride, sodium fluoride, stannous chloride, sodium silicate, tin chloride tin chloride, titanium chloride, zinc sulfate, zirconium oxychloride, and the like, and salts thereof.

As a further non-limiting example, a formulation of CDM media of the present invention comprises: sodium chloride, 3–5 g/L; potassium chloride, 0.2–0.4 g/L; , HEPES, 5–7 g/L; glucose (dextrose), 3.5–5.5 g/L; biotin, 0.000005–0.000025 g/L; ascorbic acid, 0.002–0.004; pantothenate, 0.002–0.006 g/L; choline, 0.002–0.006 g/L; folate, 0.002–0.006 g/L; inositol, 0.005–0.02 g/L; niacinamide, 0.002–0.006 g/L; pyridoxal, 0.002–0.006 g/L; riboflavin, 0.0002–0.0006 g/L; thiamine, 0.002–0.006 g/L; cyanocbalamin, 0.000005–0.000025 g/L; oxaloacetic acid, 0.1–0.4 g/L; alanine, 0.015–0.035 g/L; asparagine, 0.01–0.035 g/L; arginie, 0.06–0.10 g/L; aspartate, 0.02–0.04 g/L; cysteine, 0.3–0.5 g/L; cystine, 0.05–0.2 g/L; glutamine, 0.8–1.5 g/L; glutamate, 0.06–0.09 g/L; glycine, 0.02–0.04 g/L; histidine, 0.03–0.05 g/L; isoleucine, 0.05–0.25 g/L; leucine, 0.05–0.25 g/L: lysine, 0.05–0.25 g/L; methionine, 0.02–0.04 g/L; phenylalanine, 0.055–0.075. proline, 0.03–0.05 g/L; serine, 0.03–0.055 g/L; threonine, 0.07–0.15 g/L; tryptophan, 0.005–0.025 g/L; tyrosine, 0.05–0.15 g/L; valine, sodium selenate, 0.0000005–0.000060; magnesium sulfate, 0.05–0.2 g/L; potassium chloride, 0.15–0.45 g/L; sodium phosphate, 0.075–0.2 g/L; potassium nitrate, 0.00005–0.00009 g/L; calcium chloride, 0.08–0.25 g/L; sodium pyruvate 0.05–0.4 g/L; insulin, 0.05–2 g/L; hydrocortisone, 20–80 μg/L; linoleic acid, 1–100 mg/L; ethanolamine, 5–25 μg/L; sodium bicarbonate, 1–5 g/L; APO transferrin or ferric citrate, 1–10 mg/L; Pluronic F68, 0.2–2 g/L; sodium hydroxide, 0.3–0.9 g/L; mycophenolic acid, 0.1–2 mg/L; hypoxanthine, 2–5 mg/L; xanthine; 10–200 mg/L; sodium bicarbonate 1.5–4.5 g/L.

Known serum free hybridoma media that can be modified to provide the media of the present invention include, but are not limited to, e.g., Sigma/Aldrich product numbers S2772, S2897 and S8284 (www.sigma-aldrich.com); similar known serum free media include those from Life Technologies, Rockville, Md. (www.lifetech.com) and JRH Biosciences, Lenexa, Kans. (www jrhbio.com). For example, known serum free hybridoma cell cultures can include HEPES or MOPS, sodium bicarbonate, L-glutamine, cholesterol, insulin, BSA, transferrin or ferric citrate, in addition to other serum free mammalian cell culture components. See, e.g., SIGMA catalog, 1998, pp 1776–1777, 1677–1704, 1715–1755, 1795–1847, entirely incorporated herein by reference. Non-limiting examples of known serum free media that can be modified to provide CDM of the present invention include, but are not limited to, sigma media product numbers S2772, S2897 and S8284, as follows:

| SIGMA Prod. # Component | S 2897 g/L | S 8284 g/L | S 2772 g/L |
|---|---|---|---|
| INORGANIC SALTS | | | |
| AlCl3.6H2O | 0.000001 | 0.000001 | 0.000001 |
| NH4Vo3 | 0.0000006 | 0.0000006 | 0.0000006 |
| BaCl2 | 0.000002 | 0.000002 | 0.000002 |
| CaCl2.2H2O | 0.0441 | 0.0441 | 0.0441 |
| CoCl2.6H2O | 0.000002 | 0.000002 | 0.000002 |
| CrK(So4)2 | 0.000001 | 0.000001 | 0.000001 |
| CuSo4.5H2O | 0.0000051 | 0.0000051 | 0.0000051 |
| FeSo4.7H2O | 0.000834 | 0.000834 | 0.000834 |
| Geo2 | 0.0000005 | 0.0000005 | 0.0000005 |
| LiCl | 0.01 | 0.01 | 0.01 |
| MgCl.6H2O | 0.123 | 0.123 | 0.123 |
| MnCl(anhyd) | 0.0000001 | 0.0000001 | 0.0000001 |
| Na2Moo4.2H2O | 0.0000001 | 0.0000001 | 0.0000001 |
| NiNo3.6H2O | 0.0000002 | 0.0000002 | 0.0000002 |
| KBr | 0.0000001 | 0.0000001 | 0.0000001 |
| KCl | 0.224 | 0.224 | 0.224 |
| KI | 0.0000001 | 0.0000001 | 0.0000001 |
| RbCl | 0.00000001 | 0.00000001 | 0.00000001 |
| AgCl | 0.0000000044 | 0.0000000044 | 0.0000000044 |
| NaHCo3 | — | 2.25 | 2.25 |
| NaCl | 7.599 | 7.599 | 7.599 |
| NaF | 0.000004 | 0.000004 | 0.000004 |
| Na2HPo4(anhyd) | 0.39739 | 0.39739 | 0.39739 |
| Na2Seo3 | 0.00003 | 0.00003 | 0.00003 |
| SnCl2.2H2O | 0.0000001 | 0.0000001 | 0.0000001 |
| Tio2 | 0.000001 | 0.000001 | 0.000001 |
| ZnSo4.7H2O | 0.000863 | 0.000863 | 0.000863 |
| AMINO ACIDS | | | |
| L-Alanine | 0.009 | 0.009 | 0.009 |
| L-Arginine | 0.211 | 0.211 | 0.211 |
| L-Asparagine.H2O | 0.03401 | 0.03401 | 0.03401 |
| L-Aspartic Acid | 0.0133 | 0.0133 | 0.0133 |
| L-Citrulline | 0.005 | 0.005 | 0.005 |
| L-Cysteine.HCl.H2O | 0.035 | 0.035 | 0.035 |
| L-Glutamic Acid | 0.0147 | 0.0147 | 0.0147 |
| L-Glutamine | 0.396 | 0.396 | 0.396 |
| Glycine | 0.00751 | 0.00751 | 0.00751 |
| L-Histidine.HCl.H2O | 0.071 | 0.071 | 0.071 |
| L-Isoleucine | 0.164 | 0.164 | 0.164 |
| L-Leucine | 0.133 | 0.133 | 0.133 |
| L-Lysine.HCl | 0.109 | 0.109 | 0.109 |
| L-Methionine | 0.015 | 0.015 | 0.015 |
| L-Ornithine | 0.008 | 0.008 | 0.008 |
| L-Phenylalanine | 0.055 | 0.055 | 0.055 |

See, e.g., Ham et al., Proc. Natl. Acad. Sci. USA 53: 288–193 (1965); Myoken etal., In Vitro 25: 477–480 (1989).

More preferably, the media further comprises at least one selected from the group consisting of buffers, salts, carbohydrates, amino acids, lipids, vitamins, co-factors, and the like in suitable form. Suitable media that can be modified according to the present invention can include one or more or a combination of Iscove's modified media, Dulbecco's Modified Eagle Medium, Ham's F-12 media, e.g., as provided by SIGMA, LIFE TECHNOLOGIES OR JRH BIOSCIENCES, as listed above. Non-limiting examples, include, but are not limited to:

| Iscove's Modified Media: (Sigma I2510, I7633, I2762, I3390): | | |
|---|---|---|
| SIGMA Prod. Num. | I2510, I7633 | I2762, I3390 |
| COMPONENT | g/L | g/L |
| INORG. SALTS | | |
| CaCl2.2H2O | 0.219 | 0.219 |
| MgSO4 (anhyd) | 0.09767 | 0.09767 |
| KCl | 0.33 | 0.33 |
| KNO3 | 0.000076 | 0.000076 |
| NaHCO3 | — | 3.024 |
| KCl | 4.505 | 4.505 |
| NaH2PO4 (anhyd.) | 0.109 | 0.109 |
| Na2SeO3 | 0.000017 | 0.000017 |
| AMINO ACIDS | | |
| Alanine | 0.025 | 0.025 |
| L-Arginine.HCl | 0.084 | 0.084 |
| L-Asparagine.H$_2$O | 0.0284 | 0.0284 |
| L-Aspartic Acid | 0.03 | 0.03 |
| L-Cystine.2HCl | 0.09124 | 0.09124 |
| L-Glutamic Acid | 0.075 | 0.075 |
| L-Glutamine | 0.584 | — |
| Glycine | 0.03 | 0.03 |
| L-Histidine.HCl.H$_2$O | 0.042 | 0.042 |
| L-Isoleucine | 0.105 | 0.105 |
| L-Leucine | 0.105 | 0.105 |
| L-Lysine.HCl | 0.146 | 0.146 |
| L-Methionine | 0.03 | 0.03 |
| L-Phenylalanine | 0.066 | 0.066 |
| L-Proline | 0.04 | 0.04 |
| L-Serine | 0.042 | 0.042 |
| L-Threonine | 0.095 | 0.095 |
| L-Tryptophan | 0.016 | 0.016 |
| L-Tyrosine.2Na.2H2O | 0.10379 | 0.10379 |
| L-Valine | 0.094 | 0.094 |
| VITAMINS | | |
| D-Biotin | 0.000013 | 0.000013 |
| Choline Chloride | 0.004 | 0.004 |
| Folic Acid | 0.004 | 0.004 |
| myo-Inositol | 0.0072 | 0.0072 |
| Niacinamide | 0.004 | 0.004 |
| D-Pantothenic Acid.½Ca | 0.0004 | 0.004 |
| Pyridoxal.HCl | 0.004 | 0.004 |
| Riboflavin | 0.0004 | 0.0004 |
| Thiamine.HCl | 0.004 | 0.004 |
| Vitamin B12 | 0.000013 | 0.000013 |
| OTHER | | |
| D-Glucose | 4.5 | 4.5 |
| HEPES | 5.958 | 5.958 |
| Phenol Red.Na | 0.016 | 0.016 |
| Pyruvic Acid.Na | 0.11 | 0.11 |
| ADD | | |
| NaHCO3 | 3.024 | — |
| L-Glutamine | — | 0.584 |
| Grams of powder required to prepare 1 L | 17.7 | N/A |

See, e.g., Iscove et al., J. Exp. Med. 147: 923–933 (1978); Iscove, et al., Exp. Cell Res. 126: 121–126 (1980).

| Dulbecco's Modified Eagle's Medium (e.g., Sigma D0422, D1152, D2429, D2554, D2902, D3656, D5030, D5280, D5523). | | | | | | | | | |
|---|---|---|---|---|---|---|---|---|---|
| SIGMA Prod # COMPONENT | D0422 g/L | D1152 g/L | D2429 g/L | D2554 g/L | D2902 g/L | D3656 g/L | D5030 g/L | D5280 g/L | D5523 g/L |
| INORGANIC SALTS | | | | | | | | | |
| CaCl2.2H2O | 0.265 | 0.265 | 2.65 | 2.65 | 0.265 | 0.265 | 0.265 | 0.265 | 0.265 |
| Fe(NO3)3.9H2O | 0.0001 | 0.0001 | 0.001 | 0.001 | 0.0001 | 0.0001 | 0.0001 | 0.0001 | 0.0001 |
| MgSO4 | 0.09767 | 0.09767 | 0.9767 | 0.9767 | 0.09767 | 0.09767 | 0.09767 | 0.09767 | 0.09767 |
| KCl | 0.4 | 0.4 | 4.0 | 4.0 | 0.4 | 0.4 | 0.4 | 0.4 | 0.4 |
| NaHCO3 | 3.7 | — | — | — | — | — | | | |
| NaCl | 6.4 | 4.4 | 64.0 | 64.0 | 6.4 | 6.4 | 6.4 | 6.4 | 6.4 |
| NaH2PO4 | 0.109 | 0.109 | 1.09 | 1.09 | 0.109 | — | 0.109 | 0.109 | 0.109 |
| Succinic Acid | — | — | — | — | — | — | 0.075 | — | |
| Sodium Succinate | — | — | — | — | — | — | 0.1 | — | |
| AMINO ACIDS | | | | | | | | | |
| L-Arginine.HCl | 0.84 | 0.084 | 0.84 | 0.84 | 0.084 | 0.084 | 0.084 | 0.084 | 0.084 |
| L-Cystine.2HCl | — | 0.0626 | 0.626 | 0.626 | 0.0626 | 0.0626 | 0.0626 | 0.0626 | 0.0626 |
| L-Glutamine | 0.03 | 0.584 | 0.30 | 0.30 | 0.584 | 0.584 | — | — | 0.584 |
| Glycine | 0.042 | 0.030 | 0.42 | 0.42 | 0.030 | 0.030 | 0.030 | 0.030 | 0.030 |
| L-Histidine.HCl.H2O | 0.105 | 0.042 | 1.05 | 1.05 | 0.042 | 0.042 | 0.042 | 0.042 | 0.042 |
| L-Isoleucine | 0.105 | 0.105 | 1.05 | 1.05 | 0.105 | 0.105 | 0.105 | 0.105 | 0.105 |
| L-Leucine | 1.46 | 0.105 | 1.46 | 1.46 | 0.105 | 0.105 | 0.105 | 0.105 | 0.105 |

-continued

Dulbecco's Modified Eagle's Medium (e.g., Sigma D0422, D1152, D2429, D2554, D2902, D3656, D5030, D5280, D5523).

| SIGMA Prod # COMPONENT | D0422 g/L | D1152 g/L | D2429 g/L | D2554 g/L | D2902 g/L | D3656 g/L | D5030 g/L | D5280 g/L | D5523 g/L |
|---|---|---|---|---|---|---|---|---|---|
| L-Lysine.HCl | — | 0.146 | 0.30 | 0.30 | 0.146 | 0.146 | 0.146 | 0.146 | 0.146 |
| L-Methionine | 0.066 | 0.030 | 0.66 | 0.66 | 0.030 | 0.030 | 0.030 | 0.030 | 0.030 |
| L-Phenylalanine | 0.042 | 0.066 | 0.42 | 0.42 | 0.066 | 0.066 | 0.066 | 0.066 | 0.066 |
| L-Serine | 0.095 | 0.042 | 0.95 | 0.95 | 0.042 | 0.042 | 0.042 | 0.042 | 0.042 |
| L-Threonine | 0.016 | 0.095 | 0.16 | 0.16 | 0.095 | 0.095 | 0.095 | 0.095 | 0.095 |
| L-Tryptophan | 0.016 | — | — | 0.016 | 0.016 | 0.016 | 0.016 | 0.016 | |
| L-Tyrosine (free base) | 0.10379 | — | — | 1.0379 | 1.0379 | — | — | 0.072 | — |
| L-Tyrosine.2Na.2H2O | | 0.10379 | 0.10379 | 0.10379 | 0.10379 | — | 0.10379 | | |
| L-Valine | 0.094 | 0.094 | 0.94 | 0.94 | 0.094 | 0.094 | 0.094 | 0.094 | 0.094 |
| VITAMINS | | | | | | | | | |
| Choline Bitartrate | 0.004 | — | 0.04 | 0.04 | — | — | — | 0.0072 | — |
| Choline Chloride | 0.004 | 0.004 | — | — | 0.004 | 0.004 | 0.004 | — | 0.004 |
| Folic Acid | 0.0072 | 0.004 | 0.072 | 0.072 | 0.004 | 0.004 | 0.004 | 0.004 | 0.004 |
| myo-Inositol | 0.004 | 0.0072 | 0.04 | 0.04 | 0.0072 | 0.0072 | 0.0072 | 0.0072 | 0.0072 |
| Niacinamide | 0.004 | 0.004 | 0.04 | 0.04 | 0.004 | 0.004 | 0.004 | 0.004 | 0.004 |
| D-Pantothenic Acid.½Ca | 0.004 | 0.004 | — | — | 0.004 | 0.004 | 0.004 | 0.004 | 0.004 |
| Pyridoxal.HCl | — | 0.004 | 0.04 | 0.04 | 0.004 | 0.004 | 0.004 | 0.004 | 0.004 |
| Pyridoxine.HCl | 0.0004 | — | 0.004 | 0.004 | — | — | — | — | — |
| Riboflavin | 0.004 | 0.0004 | 0.04 | 0.04 | 0.0004 | 0.0004 | 0.0004 | 0.0004 | 0.0004 |
| Thiamine.HCl | 0.004 | 0.004 | 0.004 | 0.004 | 0.004 | 0.004 | 0.004 | 0.004 | 0.004 |
| OTHER | | | | | | | | | |
| D-Glucose | 4.5 | 4.5 | 10.0 | 45.0 | 1.0 | 4.5 | — | 1.0 | — |
| HEPES | — | 5.958 | — | — | — | — | — | — | 0.0159 |
| Phenol Red.Na | 0.0159 | 0.0159 | 0.159 | 0.159 | — | 0.0159 | — | 0.0093 | 0.11 |
| Pyruvic Acid.Na | 0.11 | — | 1.1 | 1.1 | 0.11 | — | — | 0.11 | — |
| ADD | | | | | | | | | |
| Glucose | — | — | — | — | — | 1.0 | — | — | — |
| L-Glutamine | 0.584 | — | 0.584 | 0.584 | — | — | 0.584 | 0.584 | — |
| L-Cystine.2HCl | — | — | — | — | — | — | — | — | — |
| L-Leucine | — | — | — | — | — | — | — | — | — |
| L-Lysine.HCl | — | — | — | — | — | — | — | — | — |
| L-Methionine | — | — | — | — | — | — | — | — | — |
| NaHCO3 | — | 3.7 | 3.7 | 3.7 | 3.7 | 3.7 | 3.7 | 3.7 | 3.7 |
| NaH2PO4 | — | — | — | — | — | 0.109 | — | — | — |
| Phenol Red.Na | — | — | — | — | — | — | — | — | — |
| Pyruvic Acid.Na | — | — | — | — | — | — | — | — | — |
| Grams of powder to prepare 1 L | N/A | 17.4 | N/A | N/A | N/A | N/A | N/A | N/A | 10.0 |

See, e.g., Dulbecco and Freeman, Virology 8: 396–397 (1959); Smith et al.,, J. D. Freeman, G., Vogt, M. and Dulbecco, R. (1960). Virology 12: 185–196 (1960); Morton, In Vitro 6: 89 (1970); Rutzky and Pumper, In Vitro 9: 468 (1974).

Ham's F-12/Dulbecco's Modified Eagle's Medium (e.g., Sigma D6905, D8900, D2906, D9785, D6421)

| SIGMA Prod.# COMPONENT | D6905, D8900 g/L | D2906 g/L | D9785 g/L | D6421 g/L |
|---|---|---|---|---|
| INORGANIC SALTS | | | | |
| CaCl2.2H2O | 0.1545 | 0.1545 | — | 0.1545 |
| CuSO4.5H2O | 0.0000013 | 0.0000013 | 0.0000013 | 0.0000013 |
| Fe(NO3)3.9H2O | 0.00005 | 0.00005 | 0.00005 | 0.00005 |
| FeSO4.7H2O | 0.000417 | 0.000417 | 0.000417 | 0.000417 |
| MgCl2.6H2O | 0.06120 | 0.0612 | — | 0.0612 |
| MgSO4 | 0.04884 | 0.04884 | — | 0.04884 |
| KCl | 0.3118 | 0.3118 | 0.3118 | 0.3118 |
| NaHCO3 | — | — | — | 1.2 |
| NaCl | 6.996 | 6.996 | 6.996 | 6.996 |
| Na2HPO4 | 0.07102 | 0.07102 | 0.07102 | 0.07102 |
| NaH2PO4 | 0.0543 | 0.0543 | 0.0543 | 0.0543 |

-continued

Ham's F-12/Dulbecco's Modified Eagle's Medium (e.g., Sigma D6905, D8900, D2906, D9785, D6421)

| SIGMA Prod.# COMPONENT | D6905, D8900 g/L | D2906 g/L | D9785 g/L | D6421 g/L |
|---|---|---|---|---|
| ZnSO4.7H2O | 0.000432 | 0.000432 | 0.000432 | 0.000432 |
| AMINO ACIDS | | | | |
| L-Alanine | 0.00445 | 0.00445 | 0.00445 | 0.0045 |
| L-Arginine.HCl | 0.1475 | 0.1475 | 0.1475 | 0.1475 |
| L-Asparagine.H2O | 0.0075 | 0.0075 | 0.0075 | 0.0075 |
| L-Aspartic Acid | 0.00665 | 0.00665 | 0.00665 | 0.00665 |
| L-Cystine.HCl.H2O | 0.01756 | 0.01756 | 0.01756 | 0.01756 |
| L-Cysteine.2HCl | 0.03129 | 0.03129 | 0.03129 | 0.03129 |
| L-Glutamic Acid | 0.00735 | 0.00735 | 0.00735 | 0.00735 |
| L-Glutamine | 0.365 | 0.365 | — | — |
| Glycine | 0.01875 | 0.01875 | 0.01875 | 0.01875 |
| L-Histidine.HCl.H2O | 0.03148 | 0.03148 | 0.03148 | 0.03148 |
| L-Isoleucine | 0.05447 | 0.05447 | 0.05447 | 0.5447 |
| L-Leucine | 0.05905 | 0.05905 | — | 0.05905 |
| L-Lysine.HCl | 0.09125 | 0.09125 | — | 0.09125 |
| L-Methionine | 0.01724 | 0.01724 | — | 0.01724 |
| L-Phenylalanine | 0.03548 | 0.03548 | 0.03548 | 0.03548 |
| L-Proline | 0.01725 | 0.01725 | 0.01725 | 0.01725 |
| L-Serine | 0.02625 | 0.02625 | 0.02625 | 0.02625 |
| L-Threonine | 0.05345 | 0.05345 | 0.05345 | 0.05345 |
| L-Tryptophan | 0.00902 | 0.00902 | 0.00902 | 0.00902 |
| L-Tyrosine.2Na.2H2O | 0.05579 | 0.05579 | 0.05579 | 0.05579 |
| L-Valine | 0.05285 | 0.05285 | 0.05285 | 0.05285 |
| VITAMINS | | | | |
| D-Biotin | 0.0000035 | 0.0000035 | 0.0000035 | 0.0000035 |
| Choline Chloride | 0.00898 | 0.00898 | 0.00898 | 0.00898 |
| Folic Acid | 0.00265 | 0.00266 | 0.00266 | 0.00266 |
| myo-Inositol | 0.0126 | 0.0126 | 0.0126 | 0.0126 |
| Niacinamide | 0.00202 | 0.00202 | 0.00202 | 0.00202 |
| D-Pantothenic Acid.½Ca | 0.00224 | 0.00224 | 0.00224 | 0.00224 |
| Pyridoxal.HCl | 0.002 | 0.002 | 0.002 | — |
| Pyridoxine.HCl | 0.000031 | 0.000031 | 0.000031 | 0.002031 |
| Riboflavin | 0.000219 | 0.000219 | 0.000219 | 0.000219 |
| Thiamine.HCl | 0.00217 | 0.00217 | 0.00217 | 0.00217 |
| Vitamin B-12 | 0.00068 | 0.00068 | 0.00068 | 0.00068 |

See, e.g., Barnes and Sato, Analyt. Biochem. 102:255–270 (1980).

Any suitable or desired protein for mammalian cell expression can be used in cell culture using media according to the present invention. Non-limiting examples of such proteins include, but are not limited to therapeutic or diagnostic proteins, such as eukaryotic or prokaryotic proteins. Preferred proteins can include, but art not limited to, cytokines, receptors, soluble receptors, interleukins, growth factors, and the like.

Citations

All publications or patents cited herein are entirely incorporated herein by reference as they show the state of the art at the time of the present invention and/or to provide description and enablement of the present invention. Publications refer to scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987–1999); Sambrook, et al., Molecular Cloning: A Laboratory Manual, 2$^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., N.Y. (1994–1998); Colligan et al., Current Protocols in Protein Science, John Wiley & Sons, NY, N.Y., (1997–1999).

EXAMPLES

Example 1

Production of Protein in Chemically Defined Media of the Present Invention Using Adapted Cell lines An IgG protein producing myeloma cell line named C168O was not ideally suited for commercial production of IgG or for suitable regulatory approval, due to need for media components of known serum free media containing animal protein derived preparations that were not sufficiently defined or characterized, such as Excyte and others. This Excyte dependency was not able to be alleviated by adding chemically defined lipids or other components. However, when Excyte was removed and trace elements/vitamins were supplemented, a robust growth of C168O was achieved. This medium without primatone, albumin and excyte but supplemented with trace elements and vitamins is now called "CDM". A semi-batch culture of C168O in CDM medium showed that CDM medium was able to support both high cell density growth and high IgG production.

Another myeloma cell line called C463A is capable of growing in various commercial defined media. However, this growth was not ideally suited for commercial production of IgG or for suitable regulatory approval. C463A is derived from Sp2/0 and potentially can be used as a transfection host to develop commerically suitable cell lines. In semi-batch cultures, the cell density of C463A in CDM medium of the present invention routinely reached 6 to 7 million cells per milliliter (ml) compared with 3 to 4 million per ml in other tested defined media. The viability is similar amongst all tested media (80% to 90%). Apparently, CDM has the capability to support cell growth at a higher density than other chemically defined media.

To adapt cell lines derived from Sp2/0 cells in chemically defined media is a lengthy process. It usually takes several months to one year to obtain one. When CDM medium is used, we noticed that the length of time for adaptation was much shorter than that in other defined media. In one case, it took only a few weeks to obtain CDM culture compared to several months from previous experiences.

In summary, we find that trace elements and vitamins are essential for the growth of myeloma cells in the absence of bovine serum and non-defined animal derived materials. A chemically defined formulation was generated based on the addition of trace elements and vitamins to a suitable serum free media system. This formulation provides several advantages: 1. Supports robust growth and IgG or other protein production of various myeloma and other cell lines, 2. Easy adaptation for mammalian cells, e.g., Sp2/0-derived IgG or protein producing cell lines, 3. Cost-effective since expensive components, such as bovine serum and excyte, are excluded and 4. Regulatory-friendly since potentially infectious agents are eliminated.

The use of this medium in perfusion type bioreactors is or other types of cell culture can also be used according to the present invention.

Formulation of CDM Medium:

The formulation of a CDM media of the present invention is provided as follows, e.g., Tables A-B. Table A1 shows the components added to make the media. Tables A2–A3 and B1–B4 show the listing of components for the additional formulations used in Table A1. The components are available from commercial sources, as individual components, or as custom formulations that can be ordered, e.g., from Sigma (St. Louis, Mo., USA), Aldrich (St. Louis, Mo., USA), JRH Biosciences (Lenexa, Kans., USA), and the like.

Tables A1–A3:

TABLE A1

NON-LIMITING EXAMPLE OF CDM MEDIA OF THE INVENTION

| Components | Final Concentration In Media | Physical Property | Storage Temp. |
|---|---|---|---|
| CM-2 (Part A, Table A2) | 18.8 g/l | Powder | +2–8° C. |
| CH-2 (Part B; Table A3) | 10 ml/l | Liquid | −20° C. |
| NaHCO$_3$ | 3.02 g/l | Powder | Ambient |
| Bovine APO Transferrin or ferric citrate | 5 mg/l | Stock solution Powder | +2–8° C. +2–8° C. |
| Pluronic F68 | 0.8 g/l | Stock Solution Powder Powder | +2–8° C. Ambient +2–8° C. |
| NaOH | 0.7 g/l | Stock Solution Pellets | Ambient Ambient |
| Ethanolamine | 10 or 20 mg/l | Stock Solution Liquid | −20° C. Ambient |
| Glutamine | 0.29 g/l | Powder | Ambient |
| Mycophenolic acid | 0.5 mg/l | Stock Solution WSS 2 | +2–8° C. |
| Hypoxanthine | 2.5 mg/l | | |
| Xanthine (MHX) | 50 mg/l | | |
| Hydrocortisone | 20 ug/l | WSS 9 | +2–8° C. |
| Vitamins (Table B1) | 1X | 100X Liquid | +2–8° C. |
| Trace Minerals 1 (Table B1) | 1X | 1000X Liquid | +2–8° C. |
| Trace Minerals 2 (Table B2) | 1X | 1000X Liquid | +2–8° C. |
| Trace Minerals 3 (Table B3) | 1X | 1000X Liquid | +2–8° C. |

Preparation Instructions: Add components in order listed above. The sodium hydroxide should be made the same day.
Note: Prior to pH adjustment, pH = 6.7–6.8. The density at liquid stock solutions are the same as water (p-1 g/ml). Therefore, volume or weight can be used alternatively.

S1 pH: 7.3–7.6
S1 Osm: 305–368

TABLE A2

CM-2 (Part A)

| Component | Final Conc. gm/L (Dry, 18.8 g total/L) |
|---|---|
| Sodium Chloride | 4.505 |
| Potassium Chloride | 0.330 |
| Sodium Phosphate Monobasic H$_2$O | 0.125 |
| Magnesium Sulfate, Anhydrous | 0.09767 |
| Potassium Nitrate | 0.000076 |
| Sodium Selenite | 0.0000173 |
| Calcium Chloride, Anhydrous | 0.165 |
| L-Alanine | 0.025 |
| L-Asparagine H$_2$O | 0.0284 |
| L-Arginine HCl | 0.084 |
| L-Aspartic Acid | 0.030 |
| L-Cysteine HCl H$_2$O | 0.4175 |
| L-Cystine 2HCl | 0.09124 |
| L-Glutamic Acid | 0.075 |
| L-Glutamine | 0.8763 |
| Glycine | 0.030 |
| L-Histidine HCl H$_2$O | 0.042 |
| L-Isoleucine | 0.105 |

TABLE A2-continued

CM-2 (Part A)

| Component | Final Conc. gm/L (Dry, 18.8 g total/L) |
|---|---|
| L-Leucine | 0.105 |
| L-Lysine HCl | 0.146 |
| L-Methionine | 0.030 |
| L-Phenylalanine | 0.066 |
| L-Proline | 0.040 |
| L-Serine | 0.042 |
| L-Threonine | 0.095 |
| L-Tryptophan | 0.016 |
| L-Tyrosine 2Na 2H$_2$O | 0.10379 |
| L-Valine | 0.094 |
| Dextrose | 4.500 |
| Sodium Pyruvate | 0.220 |
| Biotin | 0.000013 |
| Ascorbic Acid | 0.003 |
| D-Ca Pantothenate | 0.004 |
| Choline Chloride | 0.004 |
| Folic Acid | 0.004 |
| i-Inositol | 0.0072 |
| Niacinamide | 0.004 |
| Pyridoxal HCl | 0.004 |
| Riboflavin | 0.0004 |
| Thiamine HCl | 0.004 |
| Cyanocobalamin | 0.000013 |
| Oxalacetic Acid | 0.300 |
| HEPES | 5.958 |
| | 18.7776193 |

TABLE A3

CH-2 (Part B) (100X)

| Component | 100X: Amount/L | Final Conc. |
|---|---|---|
| Insulin | 1.0 g | 10 mg/L |
| Hydrocortisone | 200 μg | 2 μg/L |
| Linoleic Acid | 500 mg | 5 mg/L |
| Ethanolamine (1.02 mg/μl) | 1020 g | 10 mg/L |
| NaCl | 8.5 g | 85 mg/L |

CDM medium is prepared according to Table A1 by adding components CH-2, parts A (18.8 gm/L, Table A2) and B (10 ml/L (100×), Table A3), followed by NaHCO$_3$ (3.02 g/L), Bovine APO transferrin or ferric citrate (5 mg/L), Pluronic F68 (0.8 g/L), NaOH (0.7 g/L), Ethanolamine (10 μl/L), Glutamine (0.29 g/L), mycophenolic acid (0.5 mg/L), hypoxanthine (2.5 mg/L), xanthine (50 mg/L), hydrocortisone (20 μg/L), vitamins (100×, 10 ml/L, Table B 1), trace minerals 1 (1000×, 0.33–1.0 ml/L, Table B2), trace minerals 2 (1000×, 0.33–1.0 ml/L, Table B3), trace minerals 3 (1000×, 0.33–1.0 ml/L, Table B4). In this example of CDM medium of the present invention, the working concentration of trace elements is 0.33–1.00×, and 1× for vitamins.

Tables B1–B4:

TABLE B1

Vitamin Solution (100X)

| Component | Final Concentration Added(1X) mg/L | Liquid 100X mg/L |
|---|---|---|
| NaCl | 85.00 | 8500.00 |
| D-Calcium Pantothenate | 1.00 | 100.00 |
| Choline Chloride | 1.00 | 100.00 |
| Folic Acid | 1.00 | 100.00 |
| i-Inositol | 2.00 | 200.00 |
| Nicotinamide | 1.00 | 100.00 |
| Pyridoxine-HCl | 1.00 | 100.00 |
| Riboflavin | 0.1 | 10.00 |
| Thiamine-HCl | 1.00 | 100.00 |

TABLE B2

Trace Metals 1, 1000X

| COMPONENT | Final Conc. Added 0.33X µg/L | Final Conc. Added 1X µg/L | Liquid 1000X mg/L |
|---|---|---|---|
| $CuSO_4$—$5H_2O$ | 0.53 | 1.59 | 1.60 |
| $ZnSO_4$,—$7H_2O$ | 284.8 | 854.4 | 863.00 |
| Selenite-2Na | 5.7 | 17.1 | 17.30 |
| Ferric Citrate | 381.2 | 1143.6 | 1155.10 |

TABLE B3

Trace Metals 2, 1000X

| COMPONENT | Final Concentration Added (0.33X) µg/L | Final Concentration Added (1X) µg/L | Liquid 1000X mg/L |
|---|---|---|---|
| $AlCl_4$, $6H_2O$ | 0.40 | 1.20 | 1.20 |
| $AgNO_3$ | 0.056 | 0.168 | 0.17 |
| Ba $(C_2H_4O_2)_2$ | 0.842 | 2.53 | 2.55 |
| KBr | 0.040 | 0.12 | 0.12 |
| $CdCl_2$ | 0.75 | 2.25 | 2.28 |
| $CoCl_2 6H_2O$ | 0.785 | 2.355 | 2.38 |
| $CrCl_2$, (anhydeous) | 0.015 | 0.045 | 0.32 |
| NaF | 1.39 | 4.17 | 4.20 |
| $GeO_2$ | 0.175 | 0.525 | 0.53 |
| Kl | 0.056 | 0.168 | 0.17 |
| RbCl | 0.400 | 1.20 | 1.21 |
| $ZrOCl_2$ $8H_2O$ | 1.06 | 3.18 | 3.22 |

TABLE B4

Trace Metals 3, 1000X

| COMPONENT | Final Concentration Added (0.33X) µg/L | Final Concentration Added (1X) µg/L | Liquid 1000X mg/L |
|---|---|---|---|
| $MnSO_4$ $H_2O$ | 0.056 | 0.168 | 0.17 |
| $NaSiO_3$ $9H_2O$ | 46.2 | 138.6 | 140.00 |
| Molybdic Acid, Ammonium Salts | 0.409 | 1.227 | 1.24 |
| $NH_4$ $VO_3$ | 0.21 | 0.63 | 0.65 |
| $NiSO_4$ $6H_2O$ | 0.043 | 0.129 | 0.13 |
| $SnCl_2$ (anhydrous) | 0.040 | 0.120 | 0.12 |

In this experiment, a chemically defined commercial medium, CD-hybridoma, from Gibco/Life Technology was used as a reference medium. A semi-batch growth profile (a 75% media change was performed daily after Day 3 of the experiment) was initiated to determine the effects of various additives on CDM media. Data at Day 5 were used for this comparison.

TABLE I

Comparing the effects of various additives on CDM w/o PAE in a Semi-Batch Growth Profile of C463A.

| Cultures | Media Identification | Viable Cell Density (e/mL) | Total Cell Density (e/mL) | % Viability |
|---|---|---|---|---|
| A | CDM w/o OPI (oxaloacetate, pyruvate and insulin), bovine transferrin or ferric citrate and defined lipids, trace elements and vitamins | 3.24 | 5.39 | 60 |
| B | CDM in A above + OPI (oxaloacetate, pyruvate and insulin) | 1.14 | 1.90 | 60 |
| C | CDM in A above + bovine transferrin or ferric citrate and defined lipids | 3.32 | 4.68 | 71 |
| D | CDM in A above + trace elements and vitamins (CDM) | 5.22 | 6.54 | 80 |
| E | CDM in A above + OPI + transferrin or ferric citrate and defined lipids | 1.68 | 2.26 | 74 |

TABLE I-continued

Comparing the effects of various additives on CDM w/o PAE in a Semi-Batch Growth Profile of C463A.

| Cultures | Media Identification | Viable Cell Density (e/mL) | Total Cell Density (e/mL) | % Viability |
|---|---|---|---|---|
| F | CDM in A above + OPI + transferrin or ferric citrate + lipids + trace elements + vitamins | 2.74 | 3.74 | 73 |
| G | CDM in A above + 1% Sigma PFSF | 3.6 | 4.72 | 76 |
| H | LTI's CD Hybridoma media-modified | 2.64 | 3.84 | 69 |
| I | LTI's CD Hybridoma media-modified | 3.34 | 5.04 | 66 |

CDM Medium Performs Best Compared to Other Tested Chemically Defined Media

Another semi-batch growth profile experiment was initiated to compare the growth performance of C463A in CDM medium to other commercial chemically defined media. Day 3 and subsequent media change is similar to that stated in Table I.

Table II shows the results collected on Day 5 of the semi-batch experiment. The CDM culture reached the highest viable and total densities among the group. C463A viability in CDM medium was also the highest of the four cultures at 82%. The outcome of this experiment reveals that CDM medium still provides the best support for C463A growth.

TABLE II

Comparing CDM to other chemically defined commercial media in a semi-batch growth profile of C463A

| Cultures | Media Identification | Viable Cell Density (e/mL) | Total Cell Density (e/mL) | % Viability |
|---|---|---|---|---|
| A | CDHY + Sigma S8284 PFSF (50:50) | 2.47 | 3.45 | 72 |
| B | CDHY + trace elements + vitamins | 1.58 | 3.45 | 46 |
| C | CDM including + trace elements + vitamins (CDM) | 3.86 | 4.71 | 82 |
| D | LTI's CD Hybridoma media-modified | 1.52 | 4.03 | 38 |

CDM Medium supports high cell density growth and IgG production of C168O, a Remicade producing cell line.

Once CDM medium was determined to enhance growth in our new host cell line, a semi-batch experiment in spinners was initiated for C168O, a Remicade producing cell line derived from C168J (see, e.g.,. FIG. A shows that CDM can support high cell density up to $4.5 \times 10^6$ cells/mL on Day 7. In FIG. B, specific productivity for CDM culture is at 16 ug/$10^6$ cells/day. FIG. C shows that at high cell density between $4$–$5 \times 10^6$ cells/mL, IgG production reached above 60 ug/mL. Viability of the CDM spinner culture remained above 75% throughout the experiment as seen in FIG. D.

Quick Adaptation in CDM Medium

Previously, the adaptation of myeloma cell lines to defined media has been difficult and may take up to 1 year to complete. With CDM medium, the adaptation period has decreased to several weeks. Below, Table III shows another IgG-producing cell line, C380C, adapted to CDM medium in a short period of about 4–5 weeks. After C380C sustained stability in CDM medium, viability was maintained above 90% and doubling time remained within 30–35 hrs. The specific productivity and overgrown IgG titer of C380C in CDM are above that when grown in IMDM w/ 5% FBS medium.

TABLE III

Adaptation of C380C culture in CDM medium

| Media | Viability | Mean Doubling Time | Specific Productivity (ug/e/day) | Spent culture IgG titer (ug/mL) |
|---|---|---|---|---|
| IMDM w/ 5% FBS | >90% | ~22–24 hrs. | 12–13 | 55–95 |

TABLE III-continued

Adaptation of C380C culture in CDM medium

| Media | Viability | Mean Doubling Time | Specific Productivity (ug/e/day) | Spent culture IgG titer (ug/mL) |
|---|---|---|---|---|
| CDM | >90% | Now: 30–40 hrs. | 17–22 | 75–140 |

REFERENCES

Balter, M. 2000, On the hunt for a wolf in sheep's clothing. Science 287: 1906–1908

Franek, F. (1994) Starvation-Induced Programmed Death of Hybridoma Cells: Prevention by Amino Acid Mixtures. Biotechnology and Bioengineering. 45: 86–90.

Ham, R. G., and Mckeehan, W. L., 1979, Media and growth requirements, Mehhods Enzymol 58:44–93

Kozak R. W., C. F. Golker, P. Stadler, 1996, Transmissible spongiform encephalopathies : Minimizing the risk of transmission by biological/biopharmaceutical products: an industry perspective. Dev. Biol. Stand 88:257–264

Mastrangelo A. J., Shifa Zou, J. M. Hardwick, M. J. Betenbough, 1999, Antiapoptosis Chemicals Prolong Productive Lifetimes of Mammalian Cells upon Sindbis Virus Vector Infection. Biotechnology and Bioengineering. 65: 298–305.

Merten, O. -W., J. Litwin, 1991, Serum-free medium for fermentor cultures of hybridomas. Cytotechnology. 5: 69–82.

Mohamed Al-Rubeai, 1998, Apoptosis and cell cycle technology in Advances Biochemical Engineering/Biotechnology. Vol.69 pp 225–249, Springer-Verlag Berlin Heidelberg Murakami, H., H. Masui, G. H. Sato, N. Sueoka, T. P. Chow, and T. Kano-Sueoka, 1982, Growth of hybridoma cells in se serum-free medium: Ethanolamine is an essential component. Proc. Natl. Acad. Sci. USA. 79: 1158–1162.

Petch, D. and M. Butler, 1994, Profile of Energy Metabolism in a Murine Hybridoma: Glucose and Glutamine Utilization. Journal of Cellular Physiology. 161: 71–76.

Schneider, Yves-Jacques. (1988) Optimisation of hybridoma cell growth and monoclonal antibody secretion in a chemically defined serum- and protein-free culture medium. Journal of Immunological Methods. 116: 65–77.

Xie, Liangshi and Daniel I. C. Wang, 1996, High Cell Density and High Monoclonal Antibody Production Through Medium Design and Rational Control in a Bioreactor. Biotechnology and Bioengineering. 51: 725–729.

It will be clear that the invention can be practiced otherwise than as particularly described in the foregoing description and examples. Numerous modifications and variations of the present invention are possible in light of the above teachings and, therefore, are within the scope of the appended claims.

What is claimed is:

1. A chemically defined medium, said medium suitable for adaptation and growth of immortalized mammalian cells in culture to high cell densities, said medium comprising, sodium chloride, 3–5 g/L; potassium chloride, 0.2–0.4 g/L; , HEPES, 5–7 g/L; glucose (dextrose), 3.5–5.5 g/L; biotin, 0.000005–0.000025 g/L; ascorbic acid, 0.002–0.004 g/L; pantothenate, 0.002–0.006 g/L; choline, 0.002–0.006 g/L; folate, 0.002–0.006 g/L; inositol, 0.005–0.02 g/L; niacinamide, 0.002–0.006 g/L; pyridoxal, 0.002–0.006 g/L; riboflavin, 0.0002–0.0006 g/L; thiamine, 0.002–0.006 g/L; cyanocbalamin, 0.000005–0.000025 g/L; oxaloacetic acid, 0.1–0.4 g/L; alanine, 0.015–0.035 g/L; asparagine, 0.01–0.035 g/L; arginine, 0.06–0.10 g/L; aspartate, 0.02–0.04 g/L; cysteine, 0.3–0.5 g/L; cystine, 0.05–0.2 g/L; glutamine, 0.8–1.5 g/L; glutamate, 0.06–0.09 g/L; glycine, 0.02–0.04 g/L; histidine, 0.03–0.05 g/L; isoleucine, 0.05–0.25 g/L; leucine, 0.05–0.25 g/L; lysine, 0.05–0.25 g/L; methionine, 0.02–0.04 g/L; phenylalanine, 0.055–0.075 g/L; proline, 0.03–0.05 g/L; serine, 0.03–0.55 g/L; threonine, 0.07–0.15 g/L; tryptophan, 0.005–0.025 g/L; tyrosine, 0.05–0.15 g/L; valine, 0.094 g/L; sodium selenate, 0.0000005–0.000060 g/L; magnesium sulfate, 0.05–0.2 g/L; potassium chloride, 0.15–0.45 g/L; sodium phosphate, 0.075–0.2 g/L; potassium nitrate, 0.00005–0.00009 g/L; calcium chloride, 0.08–0.25 g/L; sodium pyruvate 0.05–0.4 g/L; insulin, 0.05–2 g/L; hydrocortisone, 20–80 µg/L; linoleic acid, 1–100 mg/L; ethanolamine, 5–25 µg/L; sodium bicarbonate, 1–5 g/L; APO transferrin or ferric citrate, 1–10 mg/L; Pluronic F68, 0.2–2 g/L; sodium hydroxide, 0.3–0.9 g/L; mycophenolic acid, 0.1–2 mg/L; hypoxanthine, 2–5 mg/L; xanthine; 10–200 mg/L; sodium bicarbonate 1.5–4.5 g/L.

2. The chemically defined medium of claim 1 wherein the medium is suitable for growth of immortalized mammalian cells in culture to cell densities of at least $4.5 \times 10^6$ cells/ml.

3. The chemically defined medium of claim 1 wherein the immortalized mammalian cells are the myeloma cell line Sp2/0 or derivatives thereof.

* * * * *